United States Patent [19]
Knapp et al.

[11] Patent Number: 5,725,578
[45] Date of Patent: Mar. 10, 1998

[54] TEMPORARY IMPLANT WITH TRANSPONDER AND METHODS FOR LOCATING AND INDENTIFYING

[75] Inventors: Terry R. Knapp, Neuchatel; Elizabeth Mary Belsey, Duillier, both of Switzerland

[73] Assignee: Lipomatrix Incoporated, Neuchatel, Switzerland

[21] Appl. No.: 461,117

[22] Filed: Jun. 5, 1995

Related U.S. Application Data

[63] Continuation-in-part of Ser. No. 375,811, Jan. 20, 1995, which is a continuation-in-part of Ser. No. 938,833, Aug. 31, 1992, which is a continuation-in-part of Ser. No. 221,706, Apr. 1, 1994, which is a continuation of Ser. No. 934,785, Aug. 24, 1992, Pat. No. 5,300,120.

[51] Int. Cl.⁶ .................. A61F 2/02; A61F 2/54
[52] U.S. Cl. ..................... 623/11; 623/66
[58] Field of Search ............... 623/11, 12, 18, 623/22, 23, 66, 7, 8

[56] References Cited

U.S. PATENT DOCUMENTS

| | | |
|---|---|---|
| 3,839,708 | 10/1974 | Bredesen et al. . |
| 3,949,388 | 4/1976 | Fuller . |
| 4,262,632 | 4/1981 | Hanton et al. . |
| 4,361,153 | 11/1982 | Slocum et al. ............ 128/419 P |
| 4,399,821 | 8/1983 | Bowers . |
| 4,531,526 | 7/1985 | Genest . |
| 4,618,861 | 10/1986 | Gettens et al. . |
| 4,703,756 | 11/1987 | Gough et al. . |
| 4,730,188 | 3/1988 | Milheiser . |
| 4,746,830 | 5/1988 | Holland . |
| 4,854,328 | 8/1989 | Pollack . |
| 4,863,470 | 9/1989 | Carter . |
| 4,875,483 | 10/1989 | Vollmann . |
| 4,992,794 | 2/1991 | Brouwers . |
| 5,010,893 | 4/1991 | Sholder . |
| 5,012,286 | 4/1991 | Kawano et al. . |
| 5,028,918 | 7/1991 | Giles et al. . |
| 5,036,869 | 8/1991 | Inahara . |
| 5,041,826 | 8/1991 | Milheiser . |
| 5,084,699 | 1/1992 | DeMichele . |
| 5,095,309 | 3/1992 | Troyk et al. . |
| 5,211,129 | 5/1993 | Taylor et al. . |
| 5,218,343 | 6/1993 | Stobbe et al. . |
| 5,235,326 | 8/1993 | Beigel et al. . |
| 5,300,120 | 4/1994 | Knapp et al. . |

FOREIGN PATENT DOCUMENTS

| | | |
|---|---|---|
| 0619 101 A1 | 10/1994 | European Pat. Off. . |
| WO8704900 | 8/1987 | WIPO . |
| WO9207505 | 5/1992 | WIPO . |

Primary Examiner—Debra S. Brittingham
Attorney, Agent, or Firm—Howell & Haferkamp

[57] ABSTRACT

A passive transponder may be encoded with a binary number or code of 64 bits or more and then associated with or mounted to virtually any implant intended for implantation in a human including temporary implants such as drug release implants and organ displacement devices. After implantation, the transponder's code may be conveniently read with a hand held electromagnetic reader which may merely be brought within proximity of the transponder. The encoded transponder may thus be read in a non-invasive procedure and without the use of any sophisticated or potentially harmful medical equipment or technology such as X-rays. Where the position of the implant in the human changes over time, or is otherwise unknown to attending medical personnel, the transponder and implant can be located by using a strength of signal indicator on the electromagnetic reader. The information encoded in the transponder may simply be a tag for locating the implant, or may correspond to patient demographics and implant data to aid in tracking the implant and patient for medical as well as legal reasons.

7 Claims, 5 Drawing Sheets

1

TEMPORARY IMPLANT WITH TRANSPONDER AND METHODS FOR LOCATING AND IDENTIFYING

CROSS-REFERENCE TO RELATED APPLICATIONS

This application is a continuation-in-part of copending application Ser. No. 08/375,811 filed on Jan. 20, 1995, which is a continuation-in-part of: Ser. No. 07/938,833 filed on Aug. 31, 1992; and Ser. No. 08/221,706 filed on Apr. 1, 1994, which is a continuation of Ser. No. 934,785 filed Aug. 24, 1992, now U.S. Pat. No. 5,300,120. The disclosures of all of the foregoing are incorporated herein by reference.

BACKGROUND AND SUMMARY OF THE INVENTION

With the advance of medical technology, there are a number of medical prostheses and devices which are implantable in humans for re-constructive and/or cosmetic purposes. These include breast implants; penile implants; musculature and other soft tissue implants; pace makers; valves; artificial joints and limbs such as knees, shoulders, legs, fingers, etc.; pins; screws; plates; rods; nails and other braces and supports. In order to ensure the continued safety and health of patients receiving these implants, the Safe Medical Device Act of 1990 has been enacted which dictates that manufacturers of Class III implantable medical devices institute a device registry for tracking of their devices, notification of patients, and otherwise monitoring these implants after they have been placed in a patient. Compliance with this Act has been proposed through a method of tracking which requires the surgeon who implants the device to complete and return a form or card with patient demographic data and implant data to the manufacturer or to a third party registry service. This method requires careful accumulation of data by a surgeon or his staff as well as secure inventory control procedures in order to ensure that the data is properly associated with the correct implant. Additionally, there is a risk of loss of the data entirely resulting from misdirected or lost communications. Furthermore, access to this data can be impeded in the event of an emergency situation or other circumstances which interfere with a patient's ability to recall or report the proper information which medical personnel may then use to access the registry and data contained therein.

The issues described above with respect to more permanent types of medical prosthesis and devices are very similar for devices temporarily implanted for therapeutic and other purposes, including drug release implants and organ displacement devices. An example of a drug release implant is an implant for releasing a birth control drug over a period of time, such as six months or a year. An organ displacement device is a device which is implanted into a patient, either before or after the device has been inflated with a filler material, to separate healthy organs from diseased or otherwise afflicted organs which are undergoing therapeutic treatment, such as radiation therapy. As with permanently implanted medical prosthesis and devices, temporary implants are subject to rejection, infection, and a host of other medical complications. For temporary implant patients, the ready availability of information relating to the temporary implant and the medical procedure utilized would be very helpful in treating the patient as well as in tracking and monitoring the patients progress. In emergency situations, access to this data may well be critical to proper diagnosis and treatment, especially if a disorder relating to the temporary implant is what causes the medical emergency.

There have been some suggestions in the prior art of marking the implants themselves with, for example, a radiopaque marker or other marker which contains the information relating to the implant. Ideally, this data could then be viewable by X-ray or some other non-invasive manner. However, there are difficulties with these prior art approaches. First of all, a breast implant with a radiopaque marker would at least partially obscure or mask tissue which is desired to be viewed in order to detect artifacts relating to tumors or the like for diagnosing cancer. Obviously, this is highly undesirable as the incidence of breast cancer presents a significant risk to many females. Additionally, repeated exposure to X-ray is not generally considered healthful or desirable and represents at least an added inconvenience entailing some degree of expense to recall or access the implant data. Therefore, radiopaque markers have not been viewed as a suitable long-term solution to this problem.

In order to solve these and other problems in the prior art, and in order to provide a convenient, fool proof marker associated with or secured to the implant itself, and yet readable in a non-invasive manner, the inventors herein have succeeded in designing and developing an implant which incorporates a passive transponder which may be encoded and subsequently accessed with a hand held electromagnetic reader in a quick and inexpensive procedure. The passive transponder may be secured to the implant by any convenient means. For example, in a breast implant, the multi-layered shell for the implant may be laminated around the transponder to thereby be permanently and securely fixed to the implant. The transponder may be laminated in the sidewall of the shell, or between layers which comprise the seal patch which is applied to the shell to seal the mandrel opening. Similarly, the transponder may be laminated onto the surface of most other implants in an unobtrusive location. In some other implants, the transponder may be inserted into a hole or inlay and sealed in place. Other acceptable methodologies for associating the transponder with the implant include utilizing a non-absorbable "string and basket" tether or by locating the transponder according to an "adjacent site" standard. This adjacent site may be in very close proximity to the implant or in a standardized location that may be device specific.

As passive transponders are commercially available in a cylindrical shape sized at 2 mm in diameter and 11 mm in length, the patient will not sense any discomfort or even the presence of the transponder. Also, the transponder may be encoded with any suitable encoding scheme. A commercially available transponder presently provides for the storage of up to 64 binary bits of data. This data capacity may accommodate the direct storage of much, if not all, of the information desired to be recorded and maintained in a device registry. Furthermore, the storage capacity of the transponder is expected to be increased as further development occurs over time. Alternately, a number, collection of numbers, combination of numbers and letters, or other indirect code may be stored which after reading may be used to access a data bank which itself contains the desired information. Of course, if information is directly stored in the implant, it becomes immediately available upon reading the transponder. This provides ready access to information in emergency situations. However, with the widespread availability, accessibility, and use of computers over telecommunications networks including telephone lines, it is not generally considered to be unduly limiting to provide that the code read from the transponder be then used to access an appropriate data bank in order to obtain the patient demographics, manufacturer's name, date of manufacture, surgeon's name, date of implantation, etc.

A companion hand held electromagnetic reader is also commercially available which emits a low frequency magnetic field to activate the passive transponder and thereby cause it to transmit its encoded data to the reader. With this particular commercial device, no battery or other source of electrical power need be included in the passive transponder. This further reduces the size required for the transponder and renders it particularly suitable to this application. Moreover, in the case of implants that are susceptible to movement within the patient over a period of time, or where the attending medical personnel are uncertain as to the position of the implant within the patient's body, the electromagnetic reader can be utilized for locating the transponder and implant by monitoring the strength of signal indicator provided with the reader.

While the principal advantages and features of the present invention have been described above, a more complete and thorough understanding of the invention may be attained by referring to the drawings and description of the preferred embodiment which follow.

DETAILED DESCRIPTION OF THE PREFERRED EMBODIMENT

Figure 1:
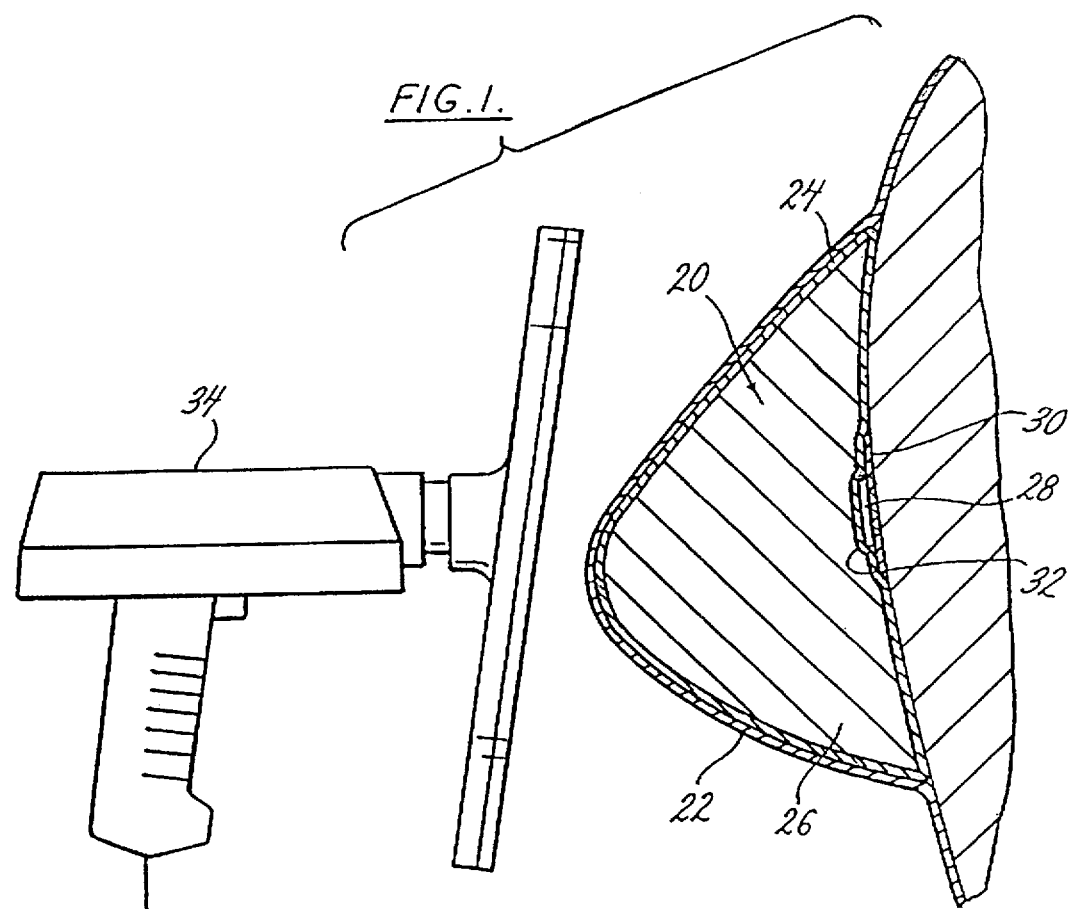
FIG. 1 is a perspective view of a breast implant containing a passive transponder with a hand held reader in position to read the encoded data contained therein.

As shown in FIG. 1, a breast implant 20 has been implanted in a female's breast 22 and includes a silicone shell 24 inflated with an appropriate fill material 26. At the posterior side of the implant 20 is shown the transponder 28 which has been laminated between adjacent layers 30, 32 of the shell 24. Transponder 28 may be any passive transponder such as a Trovan Model ID100 available from Electronic Identification Systems Ltd. of Santa Barbara, Calif. This particular transponder is designed to be environmentally independent and suitable for operation while being directly submerged in liquids. Furthermore, it may be read spherically from any direction through most materials, and including most importantly those materials comprising implants for the human body. The transponder may be directly encoded with 64 binary bits or more of data to provide almost one trillion possible different code combinations. The limit of data recorded is a function of the further progress and development of electronic memory technology. It is anticipated that FDA approval will be forthcoming for its use as part of the invention disclosed and claimed herein.

A hand held reader 34 is also shown in FIG. 1 and may be a Trovan Model LID500, or other suitable device. Its principle of operation includes emitting a low frequency magnetic field for activating the passive transponder 28. As such, transponder 28 has no power source and instead derives the energy needed for its operation from the magnetic field generated by the reader 34. This permits the transponder 28 to have a virtually unlimited life span. The hand held reader 34 is shown connected to a decoder controller 36 which accesses a data bank 38 in response to the detected code contained within transponder 28 to thereby access such data which has been stored corresponding to transponder 28. Alternately, as mentioned above, the hand held reader 34 may be used to access the code contained within transponder 28 and then other means used to access a data bank for the retrieval of the desired information. Such means might include the use of a telephone and modem to access a registry contained in a geographically centrally located site.

Figure 2:
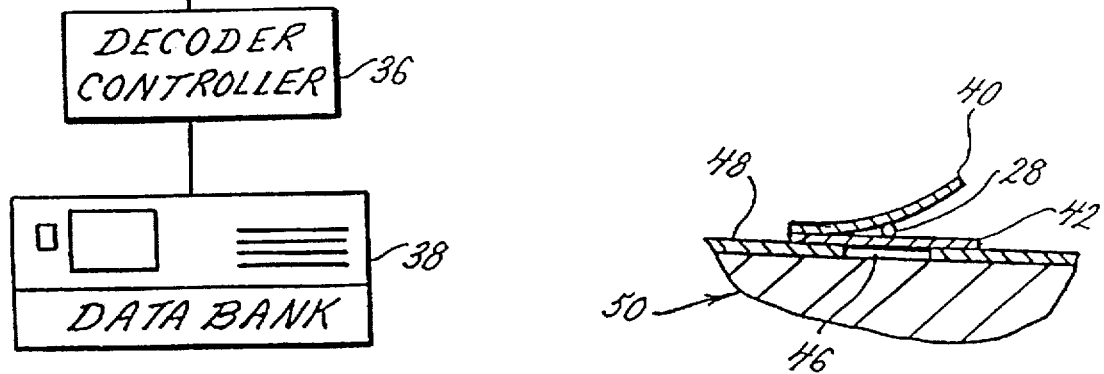
FIG. 2 is a partial cross-sectional view of the transponder as laminated between the multiple layers of a seal patch for a breast implant.

As shown in FIG. 2, the transponder 28 may be laminated between adjacent layers 40, 42 of the seal patch 44 which is commonly used to seal the mandrel opening 46 in a shell 48 of a breast implant 50. For other implants, convenient mounting locations may be readily determined with due consideration given to avoiding discomfort to the patient as well as optimizing readability of the transponder with the hand held reader.

Figure 3:
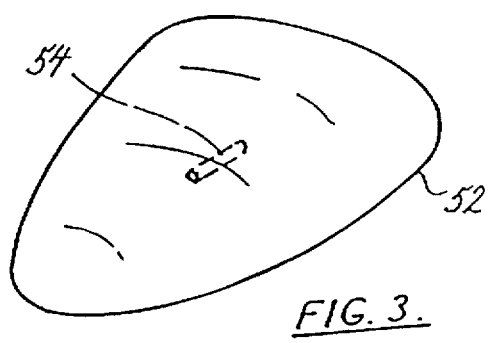
FIG. 3 is a perspective view of a pectoralis muscle implant with a passive transponder mounted therein.

As shown in FIG. 3, a pectoralis muscle implant 52 may conveniently have a passive transponder 54 contained therein. The passive transponder 54 may be molded in place, or a hole or inlay drilled for placement of the implant, after which the implant surface may then be refinished.

Figure 4:
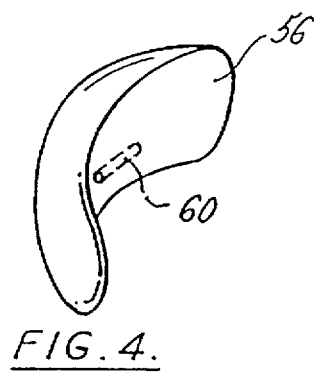
FIG. 4 is a perspective view of a soft chin implant with passive transponder mounted therein.
Figure 5:
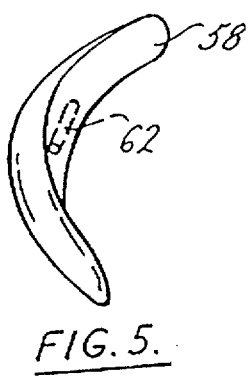
FIG. 5 is a perspective view of a rigid chin implant with a passive transponder mounted therein.
Figure 6:
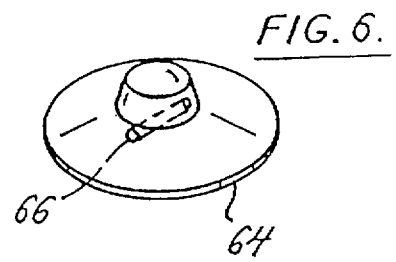
FIG. 6 is a perspective view of a nipple transplant with a passive transponder mounted therein.
Figure 7:
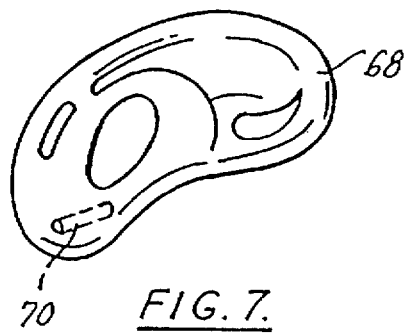
FIG. 7 is a perspective view of an otoplasty implant with a passive transponder mounted therein.
Figure 8:
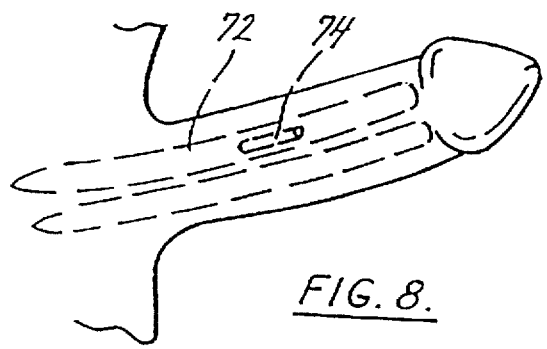
FIG. 8 is a perspective view of a penile implant, surgically implanted, with a passive transponder mounted therein.

As shown in FIGS. 4 and 5, a soft chin implant 56 or a hard chin implant 58 may also have a passive transponder 60, 62 mounted therein. As shown in FIG. 6, a nipple implant 64 has a passive transponder 66 mounted internally. In all of these transplants, the mounting of the passive transponder is achieved to provide minimal discomfort or sensation to the patient, as well as to avoid interference with the cosmetic appearance of the implant. As shown in FIG. 7, an otoplasty implant 68 may have a passive transponder 70 mounted therein. As shown in FIG. 8, a penile implant 72 may have a passive transponder 74 mounted therein.

Figure 10:
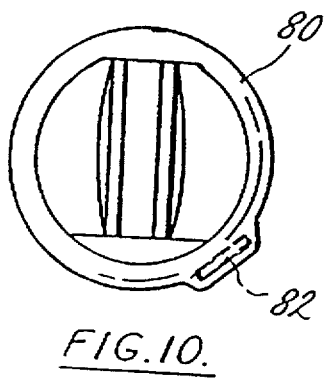
FIG. 10 is a top view of a heart valve with a passive transponder mounted to the edge thereof.
Figure 9:
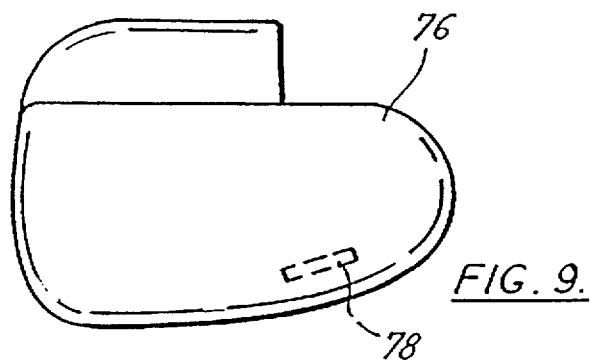
FIG. 9 is a top view of a pace maker with a passive transponder mounted thereon.

As shown in FIG. 9, a pace maker 76 may also have a passive transponder 78 mounted either on its surface or below the protective metal casing thereof. The inventors have found that reading of the passive transponder by the hand held reader may be achieved even when the transponder is obscured by metallic surfaces. As shown in FIG. 10, a heart valve 80 may have a passive transponder 82 mounted to its edge in order to avoid interference with the operability thereof, or fixation thereof.

Figure 11:
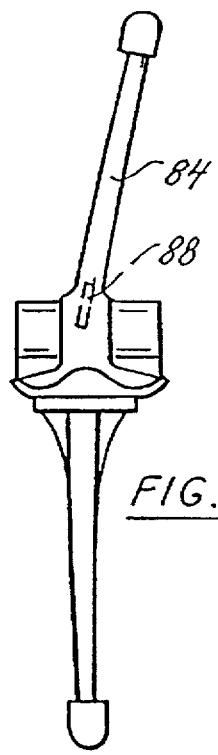
FIG. 11 is a perspective view of a total knee joint prosthesis with a passive transponder mounted thereon.
Figure 12:
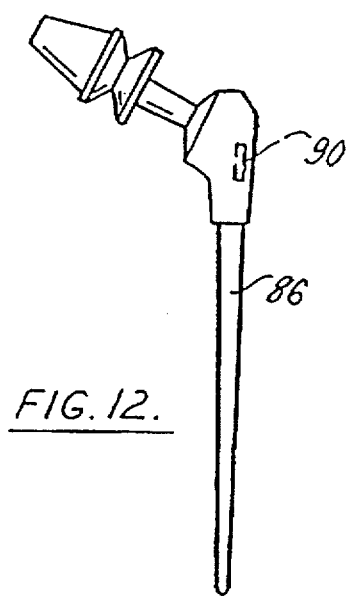
FIG. 12 is a perspective view of a shoulder arthroplasty system with a passive transponder mounted therein.

As shown in FIGS. 11 and 12, a total knee joint prosthesis 84 or a shoulder prosthesis 86, either one of which includes a majority of parts made from titanium or the like, may also conveniently carry a passive transponder 88, 90.

Figure 13:
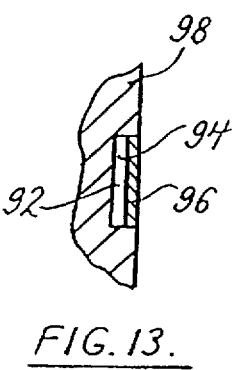
FIG. 13 is a partial cross-sectional view of a passive transponder inlaid into and below the surface of an implant.

As shown in FIG. 13, the passive transponder 92 may be placed within a trough 94 or the like and covered with a sealant 96 so that the surface of the transponder 98 is uninterrupted and smooth as is desirable in many transponders.

Figure 15:
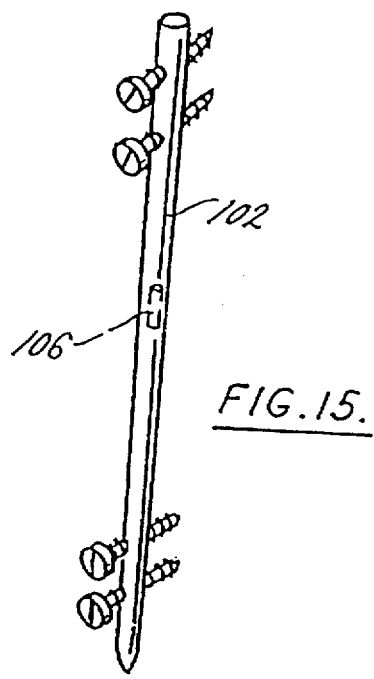
FIG. 15 is a perspective view of an orthopedic nailing system with a passive transponder mounted therein.
Figure 14:
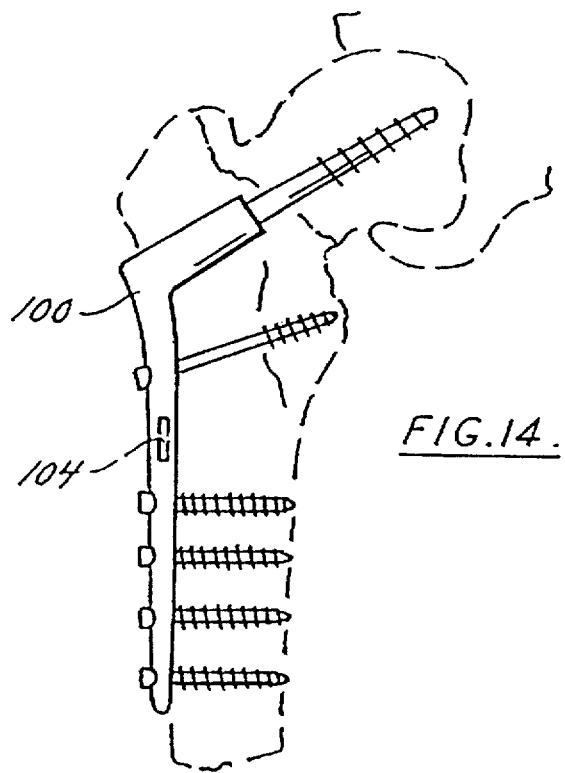
FIG. 14 is a perspective view of a femoral fixation system implanted in a femur with a passive transponder mounted thereto.
Figure 16:
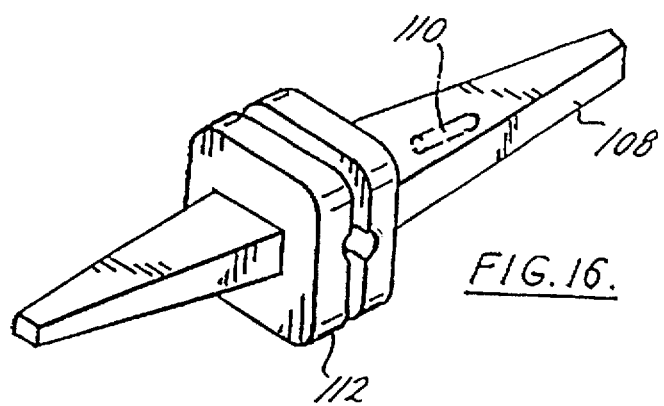
FIG. 16 is a perspective view of a finger joint prosthesis with a passive transponder mounted therein.
Figure 17:
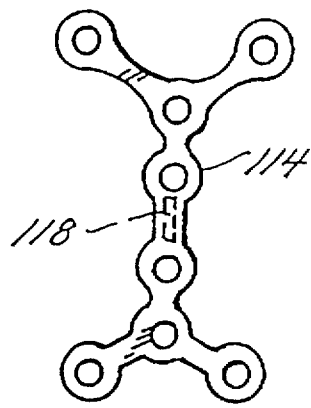
FIG. 17 is a perspective view of a craniomaxillofacial plating system with a passive transponder mounted therein.
Figure 18:
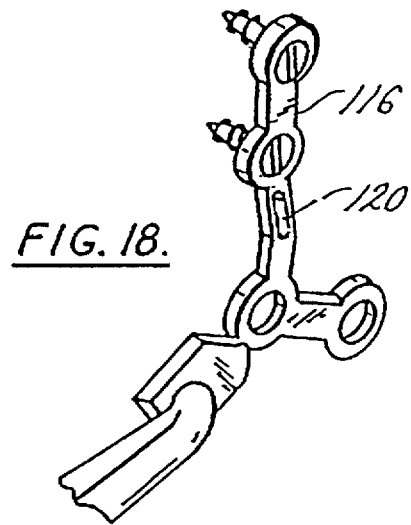
FIG. 18 is a perspective view of still another plating system with a passive transponder mounted therein.
Figure 19:
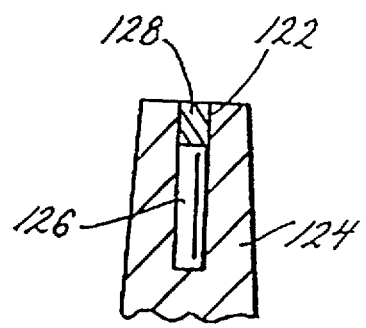
FIG. 19 is a partial cross-sectional view of a typical implant with a passive transponder mounted within a cored hole drilled therein.

As shown in FIGS. 14 and 15, a femoral fixation implant 100, or an orthopedic nailing system 102 may conveniently have a passive transponder 104, 106 inlaid therein. As shown in FIG. 16, a finger joint prosthesis 108 may also have a passive transponder 110 located in a position which does not interfere with the movable joint portion 112 of the prosthesis 108. As shown in FIGS. 17 and 18, a craniomaxillofacial plating system 114 or any other plating system 116 may also conveniently include a passive transponder 118, 120. As an alternative to the inlay mounting shown in FIG. 13, a hole 122 may be drilled in any convenient location of an implant 124 and the passive transponder 126 inserted therein and sealed in place by sealer 128, with the outer surface of sealer 128 being finished to provide a smooth surface on implant 124, as shown in FIG. 19.

Figure 20:
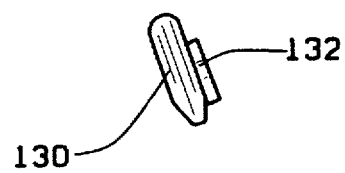
FIG. 20 is a perspective view of a drug release implant with a passive transponder affixed thereto.
Figure 21:
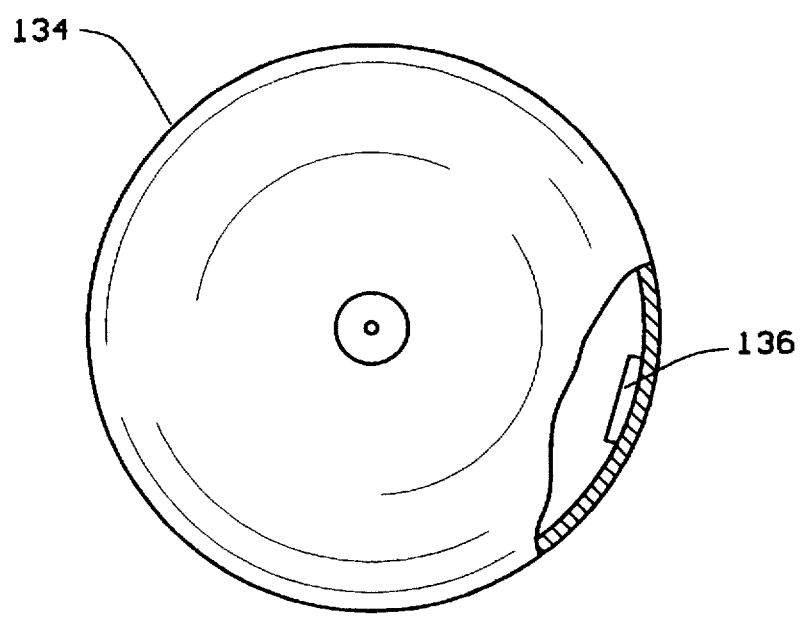
FIG. 21 is a partially cutaway view of an organ displacement device with a passive transponder mounted therein.

A passive transponder may also be utilized with implants intended for temporary implantation in humans including, but not limited to, drug release implants and organ displacement devices. As shown in FIG. 20, a drug release implant 130 may have a transponder 132 mounted thereto in such a manner that transponder 132 does not interfere with the controlled release of a drug from the implant 130. The transponder 132 may contain a code relating to information such as the date of implantation, the type of drug contained in the implant 130, and the date when the implant 130 should be removed or replaced. As shown in FIG. 21, an organ displacement device 134 may have a passive transponder 136 affixed to the interior surface of the device such that the transponder 136 does not interfere with the inflation or deflation of the organ displacement device 134, or with the therapeutic process for which the device 134 is being used. In this case, the passive transponder 136 may contain a code relating to information such as the date of implantation and the particular type of organ displacement device, as well as information pertaining to the history of the therapy undergone by the patient in which the organ displacement device is implanted.

Although all of the implants mentioned above have been described as having a passive transponder mounted to the interior or the exterior of the particular device, other acceptable methodologies for associating the transponder with the implants are available. Examples of these alternative methods include utilizing a non-absorbable string and basket tether or by locating the transponder according to an adjacent site standard. In the case of utilizing the adjacent site standard, the site may be in close proximity to the implant or in a standardized location that may be device specific.

In addition to utilizing a passive transponder in conjunction with an implant to identify the particular implant and retrieve data relating to the implant and patient, the passive transponder can also be utilized to locate the particular implant in cases where the implant is susceptible to movement within the patient's body over a period of time, or where the attending medical personnel are otherwise uncertain as to the position of the implant within the patient's body. For example, where a drug release implant is implanted into a patient for several months or years, the implant may move from the position in the patient's body where the implant was originally placed. Hence, the particular location of the implant must be ascertained before the implant can be removed. Similarly, an organ displacement device may be susceptible to movement within a patient's body during the period of time between successive therapeutic treatments. Because these devices may be inflated in situ after implantation but prior to a therapeutic treatment, and then deflated thereafter, the precise location of the organ displacement device, as well as an inflation/deflation valve associated therewith, must be ascertained prior to performing these procedures, as well as prior to removal of the device.

In these cases, the passive transponder associated with an implant can be utilized to locate the specific position of the implant in the patient's body. By utilizing an electromagnetic reader having a strength-of-signal meter, the reader can be used to externally scan over a portion of the patient's body where the implant is generally expected to be located. By referring to the strength-of-signal meter on the electromagnetic reader, the specific location of the implant can be ascertained. This specific location will correspond to the location on the patient's body where the electromagnetic reader generated the strongest read signal. In other words, as the electromagnetic reader approaches the external position of the body that corresponds to the internal location of the implant and transponder, the strength of the read signals generated by the electromagnetic reader, and indicated thereon, will increase. As the reader moves away from this external position of the body, the strength of the read signals will decrease. In this manner, the electromagnetic reader and transponder can be utilized to find an implant. Where the transponder is used in this manner for the purpose of subsequently locating the position of the implant in the patient's body, the transponder may be encoded with a simple code or tag solely for this purpose, or may additionally be encoded to identify particular information about the implant and patient, as described above.

As disclosed herein, a wide variety of implants made of all sorts of material may conveniently include a passive transponder which may be implanted, and then read by the hand held reader. This compatibility and ease of operation permits the use of a passive transponder with virtually any implant. The inventors have disclosed herein a representative sample of such implants. However, the scope of the present invention is broad enough to encompass any implant presently known to the inventors herein.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A method for identifying an implant adapted for temporary implantation in a human, said method comprising the steps of:

associating a transponder with said implant;

encoding said transponder with a unique tag corresponding to an information entry in a registry; and contemporaneously implanting said implant and said transponder in a human.

2. The method of claim 1 wherein the step of associating includes the step of physically securing said transponder to said implant so that said implant and transponder are implanted in physical proximity with each other.

3. The method of claim 1 wherein the step of associating includes the step of affixing said transponder to said implant.

4. The method of claim 1, further comprising the steps of:

externally scanning at least a portion of said human with a remote reader to generate read signals; and determining a location of said human that corresponds to a strongest read signal generated by said remote reader.

5. The method of claim 4, wherein said step of externally scanning at least a portion of the human is performed non-invasively to the human.

6. The method of claim 5, wherein the step of externally scanning at least a portion of the human is performed electromagnetically.

7. The method of claim 5, wherein the step of externally scanning at least a portion of the human further comprises the step of energizing said transponder with a remote reader, thereby to obviate a need for a battery to be contained in said transponder.

* * * * *